United States Patent [19]

Kohn et al.

[11] Patent Number: 4,467,092
[45] Date of Patent: Aug. 21, 1984

[54] CARBAMATES AND THIOCARBAMATES OF 3-HYDROXY-4-PYRIDYLOXYPHENOXY ALKANOIC ACID ESTERS

[75] Inventors: Gustave K. Kohn, Palo Alto; Joe T. Bamberg, Redwood City, both of Calif.

[73] Assignee: Zoecon Corporation, Palo Alto, Calif.

[21] Appl. No.: 410,174

[22] Filed: Aug. 20, 1982

[51] Int. Cl.$^3$ .......................................... C07D 213/64
[52] U.S. Cl. ................................... 546/291; 544/354; 546/157; 548/166; 548/221; 560/41; 560/43; 560/63
[58] Field of Search ........................................ 546/291

[56] References Cited

U.S. PATENT DOCUMENTS

| | | | |
|---|---|---|---|
| 3,379,752 | 4/1968 | Bolhofer | 260/473 |
| 4,134,751 | 1/1979 | Nishiyama et al. | 71/94 |
| 4,216,007 | 8/1980 | Nishiyama et al. | 71/94 |
| 4,348,221 | 9/1982 | Szczepanski et al. | 71/94 |
| 4,375,546 | 3/1983 | Pawloski et al. | 546/292 |

*Primary Examiner*—Alan L. Rotman
*Attorney, Agent, or Firm*—Jacqueline S. Larson; Donald W. Erickson

[57] ABSTRACT

N-alkyl (aryl) carbamates and thiocarbamates of 3-hydroxy-4-substituted phenoxy alkanoic acid esters which are useful for the control of weeds.

5 Claims, No Drawings

CARBAMATES AND THIOCARBAMATES OF 3-HYDROXY-4-PYRIDYLOXYPHENOXY ALKANOIC ACID ESTERS

This invention relates to novel carbamates of 3-hydroxy-4-substituted phenoxy alkanoic acid esters which are useful herbicides.

The novel compounds of the present invention are represented by the following formula (A):

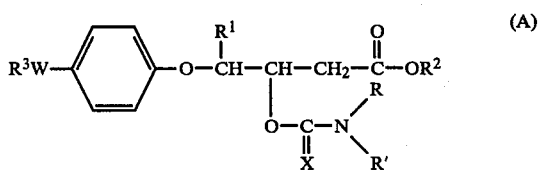

wherein,
R is lower alkyl or aryl;
R' is hydrogen or lower alkyl;
$R^1$ is hydrogen or lower alkyl;
$R^2$ is lower alkyl, lower alkenyl or lower alkynyl;
W is oxygen, sulfur or amino;
X is oxygen or sulfur; and
$R^3$ is one of the groups

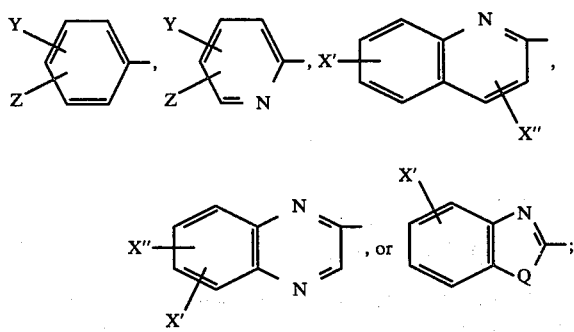

in which,
each of Y and Z is independently selected from hydrogen, lower alkyl, lower haloalkyl, lower alkoxy, lower haloalkoxy, bromo, chloro, fluoro, nitro and cyano;
each of X' and X" is independently selected from hydrogen, fluoro, chloro, bromo, trifluoromethyl, methoxy or nitro, provided that both X' and X" cannot be trifluoromethyl, methoxy or nitro; and Q is oxygen or sulfur.

In the description and claims hereinafter, each of R', R—$R^3$, Q, W, X, X', X", Y and Z is as defined above, unless otherwise specified.

The compounds of formula (A) can be synthesized by the reaction of an isocyanate or thioisocyanate (RNCX) or a carbamoyl chloride or thiocarbamoyl chloride (RR'NCXCl) with a 3-hydroxy compound of formula (I). The reaction can be carried out in an inert solvent with a tertiary amine as catalyst.

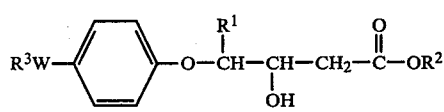

Examples of isocyanates and carbamoyl chlorides which can be used in the foregoing reaction are methyl isocyanate, 2-methylpropyl isocyanate, ethylisocyanate, 3,4-dichlorophenyl isocyanate, 4-chlorophenyl isocyanate, phenyl isocyanate, butylethylcarbamoyl chloride, dipropylcarbamoyl chloride, 4-cyanophenyl carbamoyl chloride, 4-nitrophenylcarbamoyl chloride, 3-chlorophenylcarbamoyl chloride, and the like.

The starting materials of formula (I) can be prepared by methods described by Shy-Fuh Lee, European Patent Aplication No. 81304703 (Pub. No. 0050019), the disclosure of which is incorporated herein by reference.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "aryl" refers to the group phenyl or phenyl substituted with a,e.g., chloro, cyano, nitro, lower alkyl or lower haloalkyl group.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds such as green foxtail, watergrass, shattercane Johnson-grass and the like.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broadspectrum postemergence weed control in most broadleaf crops. Examples of herbicides which can be combined with a compound of the present invention include glyphosphate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox, and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

To ethyl 4-[4-(4-trifluoromethylphenoxy)phenoxy]-3-hydroxypentanoate (1.9 g) in ethyl ether (10 ml) is added methyl isocyanate (3 ml) followed by pyridine (5 drops). The reaction mixture is refluxed for 3 hours. Then, additional methyl isocyanate (3 ml) is added and the mixture refluxed for about 3 hours. After cooling, the mixture is concentrated by evaporation under vacuum and the concentrate is purified by column chromatography (silica gel) eluting with hexane/ethyl acetate (4:1). Fractions 11–20 are collected to yield the desired N-methyl carbamate (II, R=CH$_3$, R'=H, R$^2$=CH$_2$CH$_3$, X=O, Y=H, Z=CF$_3$).

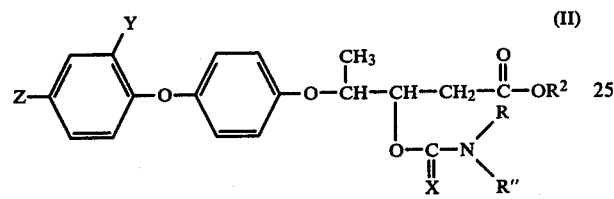

EXAMPLE 2

A mixture of ethyl 4-[4-(4-trifluoromethylphenoxy)phenoxy]-3-hydroxypentanoate (1.71 g), phenyl isocyanate (1.1 equiv.), ethyl ether (20 ml) and pyridine (5 drops) is refluxed for five hours. The reaction is worked up as in Example 1 (collecting fractions 2 and 3) to yield the N-phenyl carbamate (II; R=phenyl, R'=H, R$^2$=CH$_2$CH$_3$, X=O, Y=H, Z=CF$_3$).

EXAMPLE 3

Following the procedure of Example 1, each of diethylcarbamoyl chloride and methyl thioisocyanate is reacted with ethyl 4-[4-(4-trifluoromethylphenoxy)phenoxy]-3-hydroxypentanoate to yield, respectively, the N,N-diethyl carbamate (II; R=CH$_2$CH$_3$, R'=CH$_2$CH$_3$, R$^2$=CH$_2$CH$_3$, X=O, Y=H, Z=CF$_3$) and the N-methyl thiocarbamate (II; R=CH$_3$, R'=H, R$^2$=CH$_2$CH$_3$, X=S, Y=H, Z=CF$_3$).

EXAMPLE 4

Each of the 3-hydroxy compounds under column I is reacted with methyl isocyanate using the process of Example 1 to yield the corresponding N-methyl carbamate.

I

1. Ethyl 4-[4-(5-trifluoromethyl-2-pyridyloxy)phenoxy]-3-hydroxypentanoate.
2. Ethyl 4-[4-(3-chloro-5-trifluoromethyl-2-pyridyloxy)phenoxy]-3-hydroxypentanoate.
3. Ethyl 4-[4-(3,5-dichloro-2-pyridyloxy)phenoxy]-3-hydroxypentanoate.
4. Methyl 4-[4-(2-chloro-4-trifluoromethylphenoxy)phenoxy]-3-hydroxypentanoate.
5. Ethyl 4-[4-(2,4-dichlorophenoxy)phenoxy]-3-hydroxypentanoate.

What is claimed is:

1. A compound of the following formula (A):

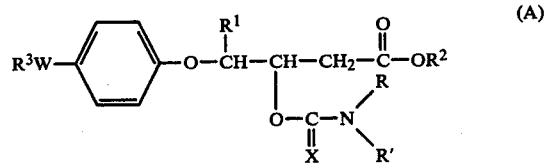

wherein,
R is lower alkyl or unsubstituted phenyl;
R' is hydrogen or lower alkyl;
R$^1$ is hydrogen or lower alkyl;
R$^2$ is lower alkyl, lower alkenyl or lower alkynyl;
W is oxygen;
X is oxygen or sulfur; and
R$^3$ is

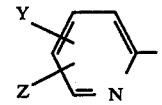

in which,
each of Y and Z is independently selected from hydrogen, trifluoromethyl, bromo, chloro and fluoro.

2. A compound according to claim 1 wherein R$^1$ is methyl, R$^2$ is lower alkyl, X is oxygen and R$^3$ is the group

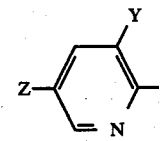

in which Y is hydrogen or chloro and Z is chloro or trifluoromethyl.

3. A compound according to claim 2 wherein each of Y and Z is chloro, R is methyl or phenyl and R' is hydrogen.

4. A compound according to claim 2 wherein Z is trifluoromethyl, R is methyl or phenyl and R' is hydrogen.

5. The compound according to claim 4 wherein R$^2$ is ethyl, Y is chloro and R is methyl.

* * * * *